(12) United States Patent
Le Grognec et al.

(10) Patent No.: US 9,724,673 B2
(45) Date of Patent: Aug. 8, 2017

(54) SUPPORTED ALKOXYLATED ORGANOTIN REACTANT, PREPARATION AND USE FOR HETEROGENEOUS-PHASE SYNTHESIS OF TETRAZOLES

(75) Inventors: Erwan Le Grognec, Lorient (FR); Jean-Paul Quintard, La Chapelle sur Erdre (FR); Gaelle Kerric, Merlevenez (FR); Jean-Mathieu Chretien, Argentre (FR); Francoise Zammattio, Coueron (FR)

(73) Assignees: UNIVERSITE DE NANTES, Nantes (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 555 days.

(21) Appl. No.: 14/129,355

(22) PCT Filed: Jun. 27, 2012

(86) PCT No.: PCT/FR2012/051480
§ 371 (c)(1),
(2), (4) Date: Apr. 1, 2014

(87) PCT Pub. No.: WO2013/001235
PCT Pub. Date: Jan. 3, 2013

(65) Prior Publication Data
US 2014/0206825 A1    Jul. 24, 2014

(30) Foreign Application Priority Data

Jun. 30, 2011  (FR) ...................... 11 02058

(51) Int. Cl.
| | | |
|---|---|---|
| *B01J 23/14* | (2006.01) | |
| *C07D 257/04* | (2006.01) | |
| *C08F 8/42* | (2006.01) | |
| *C08F 8/26* | (2006.01) | |
| *C07F 7/22* | (2006.01) | |

(52) U.S. Cl.
CPC ............ *B01J 23/14* (2013.01); *C07D 257/04* (2013.01); *C07F 7/2232* (2013.01); *C08F 8/26* (2013.01); *C08F 8/42* (2013.01)

(58) Field of Classification Search
CPC .......... B01J 23/14; B01J 35/02; B01J 35/026; C07F 7/2208; C07F 7/2232; C07F 9/6524; C07D 257/04; C08F 8/42
USPC ................ 525/333.3, 370; 502/152; 548/250
See application file for complete search history.

(56) References Cited

U.S. PATENT DOCUMENTS

| | | | |
|---|---|---|---|
| 5,399,578 A | 3/1995 | Buehlmayer et al. | |
| 5,629,331 A | 5/1997 | Caron et al. | |

FOREIGN PATENT DOCUMENTS

EP    0 708 103    4/1996

OTHER PUBLICATIONS

Matlin et al., J. Chem. Soc., Chem. Commun., 1984, Issue 12, pp. 798-799.*
Cantillo et al., J. Am. Chem. Soc. 133 (2011) 4465-4475.*
International Search Report dated Aug. 20, 2012, corresponding to PCT/FR2012/051480.
J.M. Chretien, et al.; "Preparation of Allyltin Reagents Graftedon SolidSupport: Clean and Easily Recyclable Reagents for Allylation of Aldehydes"; vol. 12, Jun. 6, 2006, pp. 6816-6828.
G. Kerric, et al.; "Synthesis, Characterization and Primary Evaluation of the Synthetic Efficiency of Supported Vinyltins and Allyltins"; vol. 695, No. 9; May 1, 2010; pp. 1414-1424.
Curran, et al.; Tris(2-Perfluorohexylethyl)tin azide: A new reagent for preparation of 5-substituted tetrazoles from nitriles with Purification by Fluorous/Organic Liquid-Liquid Extraction; vol. 55, No. 29; Jul. 16, 1999.

* cited by examiner

*Primary Examiner* — Roberto Rabago
(74) *Attorney, Agent, or Firm* — Ipsilon USA, LLP (57) ABSTRACT

A supported alkoxylated organotin reactant, to the process for preparing same, to the use of such a reactant as a catalyst for heterogeneous-phase organic synthesis, and also to a process for heterogeneous-phase synthesis of 5-substituted or 1,5-disubstituted tetrazoles using such a reactant.

9 Claims, 2 Drawing Sheets

SUPPORTED ALKOXYLATED ORGANOTIN REACTANT, PREPARATION AND USE FOR HETEROGENEOUS-PHASE SYNTHESIS OF TETRAZOLES

The present invention relates to a supported alkoxylated organotin reactant, the method of preparation thereof, the use of such a reactant as catalyst for heterogeneous-phase organic synthesis, as well as a method of heterogeneous-phase synthesis of 5-substituted or 1,5-disubstituted tetrazoles using said reactant.

The tetrazole function is a chemical function that occurs in numerous molecules having applications in various fields such as explosives, photography, agrochemistry, and pharmacy. In the pharmaceutical field, we may mention in particular as an example the family of sartans, which are angiotensin II antagonists, used for treating cardiovascular diseases as well as the cyclooxygenase 2 (COX-2) inhibitors, which are anti-inflammatories.

It is essential for companies producing and marketing molecules having one or more tetrazole functions, and notably for pharmaceutical laboratories, to be able to synthesize them efficiently, safely (for the personnel and for the environment), at an acceptable cost price and with the highest possible purity notably with respect to residual metal contents.

Compounds with a tetrazole function can be synthesized by various methods. It is possible for example to use methods employing hydrazoic acid ($HN_3$), which is however a toxic and explosive gas that is dangerous to handle. It is also possible to use methods involving a metal nitride (Na, Al, B, Si, etc.), which reacts with a nitrile corresponding to the tetrazole that we wish to obtain, optionally in the presence of a Lewis acid. Thus, a method of synthesis of a derivative having a tetrazole function by reaction of a corresponding nitrile with an alkali-metal nitride such as sodium nitride and triethylamine hydrochloride has already been proposed, notably in patent application EP-A1-0 708 103. In this case, synthesis takes place in the liquid phase and additional purification steps, for example by crystallization, are necessary to isolate the expected derivative having a tetrazole function, which leads to extra production costs. It is also possible to synthesize molecules having a tetrazole function using organotin derivatives such as trialkyl- or triaryltin nitrides as described for example in U.S. Pat. No. 5,399,578. However, although the use of organotin nitrides allows efficient synthesis of molecules having a tetrazole function, its advantages are, however, outweighed by the need to carry out difficult purifications for the tin residues to be separated completely from the tetrazoles synthesized, which also leads to extra costs of synthesis.

There is therefore a need for a reactant usable as catalyst and which notably makes it possible to synthesize compounds with a tetrazole function by a method that is both efficient and economical, in particular by a method in which recovery of the products synthesized is facilitated while avoiding as far as possible contamination of them with tin residues.

The present invention therefore relates to an alkoxylated organotin reactant of the following formula (I):

in which:
Sup represents a macromolecular solid support, preferably insoluble in organic solvents;
Z represents a linkage between the macromolecular solid support Sup and the tin atom, Z being selected from the groups of the following formulas (Z-1) to (Z-6):

in which:
n and m, independently of one another, are integers in the range from 2 to 24, and preferably from 3 to 12,
o and p, independently of one another, are integers in the range from 1 to 24, and preferably from 1 to 12
q is an integer in the range from 1 to 24 and preferably from 1 to 2,
$R^1$, $R^2$ and $R^3$, independently of one another, represent a linear $C_1$-$C_{24}$ alkyl radical, a branched or cyclic $C_3$-$C_{24}$ alkyl radical, linear $C_2$-$C_{24}$ alkenyl, branched or cyclic $C_3$-$C_{24}$ alkenyl; aryl or aralkyl.

The polymer of the solid support can be selected from the styrene-based polymers such as polystyrenes, crosslinked polystyrenes, butadiene/styrene, acrylonitrile/butadiene/styrene or methyl methacrylate/butadiene/styrene copolymers, poly(phenylene ethers), poly(phenylene sulfides), and polyamides.

It has been demonstrated that crosslinked polystyrenes are particularly indicated as support for the heterogeneous catalysts of the present invention. In this case, the polystyrenes can be obtained by copolymerization of styrene and a crosslinking agent. As crosslinking agent, we may notably mention for example ethane-1,2-diol methacrylate, propane-1,2,3-triol methacrylate, butadiene, trivinylbenzene and divinyltoluene, divinylbenzene, the latter being particularly preferred according to the invention.

Said polymer support is preferably insoluble in the organic solvents used in organic synthesis and notably for synthesis of the tetrazoles. Such a support is nevertheless capable of interacting with said solvent, and in particular, these polymers, whether they are macroporous or microporous, swell to a varying extent depending on the nature of the solvent used.

A polymer support particularly preferred according to the invention is selected from the polymer supports resulting from the copolymerization of styrene and divinylbenzene as crosslinking agent.

Among the alkyl radicals mentioned for $R^1$, $R^2$, $R^3$, the radicals preferably correspond to methyl, ethyl, n-propyl, isopropyl, n-butyl, 2-butyl, isobutyl, tert-butyl, n-pentyl, iso-pentyl, neo-pentyl, tert-pentyl, hexyl, n-octyl, iso-octyl, 2-ethyl-1-hexyl, 2,2,4-trimethylpentyl, nonyl, decyl, dodecyl, cyclopentyl, cyclohexyl, cycloheptyl, methylcyclohexyl, the most favorable substituents being methyl, ethyl, n-propyl, isopropyl and n-butyl.

Among the alkenyl radicals mentioned above for $R^1$, $R^2$, and $R^3$, we may mention in particular the vinyl, 1-propenyl, 2-propenyl and butenyl radicals.

The aryl radicals mentioned above for $R^1$, $R^2$ and $R^3$ correspond to a monocyclic or polycyclic aromatic hydrocarbon group, optionally mono- or polysubstituted. As aryl radical, we may mention in particular the naphthyl, anthranyl, phenanthryl, o-tolyl, p-tolyl, xylyl, ethylphenyl, mesityl, phenyl and benzyl groups.

According to a preferred embodiment of the invention, the reactants of formula (I) are selected from the compounds in which:

Sup is a polymer solid support based on crosslinked or noncrosslinked styrene;

$Z=-(CH_2)_n$ with n=3 or 4; and the radicals $R^1$, $R^2$, and $R^3$ have the following meanings.
  i) $R^1=R^2=R^3$=methyl, ethyl, propyl or butyl;
  ii) $R^1=R^2$=methyl and $R^3$=ethyl, propyl or butyl;
  iii) $R^1=R^2$=ethyl and $R^3$=methyl, propyl or butyl;
  iv) $R^1=R^2$=propyl and $R^3$=methyl, ethyl or butyl; or
  v) $R^1=R^2$=butyl and $R^3$=methyl, propyl or ethyl.

The present invention also relates to a method of preparing an alkoxylated organotin reactant of formula (I) as described above, said method being characterized in that it comprises at least the following steps:

1) a first step of reacting, in an organic solvent, a solid support of the following formula (II):

Sup-Z—$R^4$ (II)

in which:

Sup is a macromolecular solid support as defined above for the reactants of formula (I), said support being insoluble in said organic solvent;

Z has the same meaning as that stated above for the reactants of formula (I), $R^4$ represents a halogen atom such as chlorine, bromine, or a sulfonate group selected from the mesylate, triflate and arylsulfonate groups;

with an organotin compound of the following formula (III):

$R^1R^2SnArM$ (III)

in which:

$R^1$ and $R^2$ have the same meaning as that stated above for the reactant of formula (I), Ar is a substituted or unsubstituted phenyl group, M is a metal selected from lithium, sodium, potassium, magnesium and copper to obtain a supported organotin compound of the following formula (IV):

(IV)

in which Sup, Z, $R^1$, $R^2$ and Ar have the same meaning as that stated above for the compounds of formulas (II) and (III);

2) a second step, consisting of reacting the compound of formula (IV) obtained above at the end of the first step, in an organic solvent, with a compound of formula $X_2$ selected from $I_2$, ICl, $Cl_2$ and $Br_2$ or with a Brønsted acid of formula HX in which $X=Cl^-$, $Br^-$, $CF_3COO^-$, $ArSO_3^-$, or $RCOO^-$ with R=alkyl or aryl, to obtain a compound of the following formula (V):

(V)

in which Sup, Z, $R^1$ and $R^2$ have the same meaning as that stated above for the compounds of formulas (II) and (III) and X is as defined above; and 3) a third step, consisting of introducing the compound of formula (V) obtained above in the second step in an aqueous-alcoholic solvent in the presence of a strong base, stirring the resultant mixture for a period of from 6 to 24 hours; and then adding a carbonate of the following formula (VI):

(VI)

in which the radicals $R^3$ are identical and have the same meaning as that stated above for the reactants of formula (I), to obtain the expected reactant of formula (I).

The solid supports of formula (II) usable in the first step can easily be obtained by functionalization of a polymer support Sup with a linkage Z, and then with the tin part according to the conventional methods that are well known by a person skilled in the art.

The polymer support Sup is generally in the form of particles of variable size.

As solid support of formula (II), we may notably mention the supports of polystyrene, crosslinked for example with divinylbenzene. Such a support corresponds for example to the product known by the trade name Amberlite® XE 305 from the company Rohm and Haas or the product PL-PS/DVB MP Resin marketed by Polymer Laboratories. These commercial products are then functionalized for example with chlorobutyl groups (to obtain a linkage of type Z-1 with n=4) by methods already described in the literature.

The organotin compounds of formula (III) are known products. Their method of preparation is described for example starting from a compound of formula $R^1R^2SnArX$ and lithium or else starting from a compound of formula $R^1R^2SnArH$ and lithium diisopropylamide in tetrahydrofuran (THF) or else starting from a compound of formula $R^1R^2SnArH$ and sodium hydride or potassium hydride in THF or dimethoxyethane (DME).

The solvent used in the first step is preferably selected from tetrahydrofuran (THF), 2-methyl-tetrahydrofuran, dimethoxyethane (DME), and dioxane. Among these solvents, THF is particularly preferred.

The first step is preferably carried out at a temperature gradually increasing from 0° C. to 25° C. for a time of 16 to 24 hours.

The organic solvent used during the second step is preferably selected from the lower alcohols such as ethanol, isopropanol or propanol. Ethanol is particularly preferred.

The second step is preferably carried out at a temperature ranging from 40 to 80° C. for 12 to 24 hours.

The aqueous-alcoholic solvent used in the third step is preferably selected from mixtures of water and at least one lower alcohol such as ethanol for example.

The third step is preferably carried out at a temperature between 80 and 140° C. (depending on the nature of $R^3$) for a period of from 6 to 24 hours.

When the synthesis has ended, the reactant of formula (I) thus obtained can easily be separated from the reaction mixture in which it was synthesized and in which it is insoluble, for example by filtration, decanting or sedimentation, etc.

The alkoxylated organotin compounds of formula (I) can advantageously be used for catalyzing the heterogeneous-phase synthesis of organic compounds.

The present invention therefore also relates to the use of an alkoxylated organotin compound of formula (I) as defined above, as catalyst, in a method of heterogeneous-phase synthesis of organic compounds, in particular for catalyzing the synthesis of 5-substituted or 1,5-disubstituted tetrazoles.

The invention finally relates to a method of heterogeneous-phase synthesis of tetrazoles of the following formulas (XIIIa) and (XIIIb):

(XIIIa)

(XIIIb)

in which:
$R^5$ represents a hydrogen atom or a protective group;
$R^6$ represents a linear $C_1$-$C_{24}$ alkyl radical, a branched or cyclic $C_3$-$C_{24}$ alkyl radical; a substituted or unsubstituted aryl, aralkyl or heteroaryl group;
characterized in that said method comprises:
1) at least one first step consisting of reacting, in an organic solvent, under inert atmosphere and at a temperature greater than or equal to 110° C., a nitrile of the following formula (VIII):

$$R^6-CN \quad \text{(VIII)}$$

in which $R^6$ has the same meaning as that stated above for the compounds of formula (XIIIa) and (XIIIb), with a tin nitride of the following formula (X):

(X)

in which Sup, Z, $R^1$ and $R^2$ have the same meaning as that stated above for the compounds of formula (I) above, said reactant of formula (X) being generated in situ by reaction of the corresponding alkoxylated organotin reactant of formula (I) as defined above and a trialkylsilyl nitride of the following formula (IX):

(IX)

in which the radicals $R^7$, $R^8$ and $R^9$, which may be identical or different, represent a linear $C_1$-$C_{12}$ (preferably $C_1$-$C_4$) alkyl radical or a branched or cyclic $C_3$-$C_{12}$ alkyl radical,
to obtain a tetrazole of the following formulas (XIIa) or (XIIb):

(XIIa)

(XIIb)

in which $R^6$ has the same meaning as in formula (VIII) above and $R^7$, $R^8$ and $R^9$ have the same meaning as in formula (IX) above, after a reaction of exchange of the stannyl tetrazoles of the following formulas (XIa) or (XIb):

(XIa)

(XIb)

in which the radicals $R^1$, $R^2$ and $R^6$ have the same meanings as those stated above for the compounds of formulas (X) and (VIII) respectively, with the compound of formula (IX), and 2) at least one second step consisting:
i) either of hydrolyzing the compound of formulas (XIIa) or (XIIb) obtained above in step 1) in an acid medium, to obtain a compound of formulas (XIIIa) or (XIIIb) as defined above in which $R^5$ is a hydrogen atom,
ii) or, when we wish to obtain a compound of formula (XIIIa) or (XIIIb) in which $R^5$ is different from a hydrogen atom, of reacting said compound of formula (XIIa) or (XIIb) obtained above in step 1) with a halide of the following formula (XIV):

in which X' is a halogen atom selected from chlorine and bromine and iodine and $R^5$ has the same meaning as that stated above for the compounds of formulas (XIIIa) and (XIIIb), to obtain a compound of formula (XIIIa) or (XIIIb) in which $R^5$ has the same meaning as in formula (XIV) above.

Figure 1:
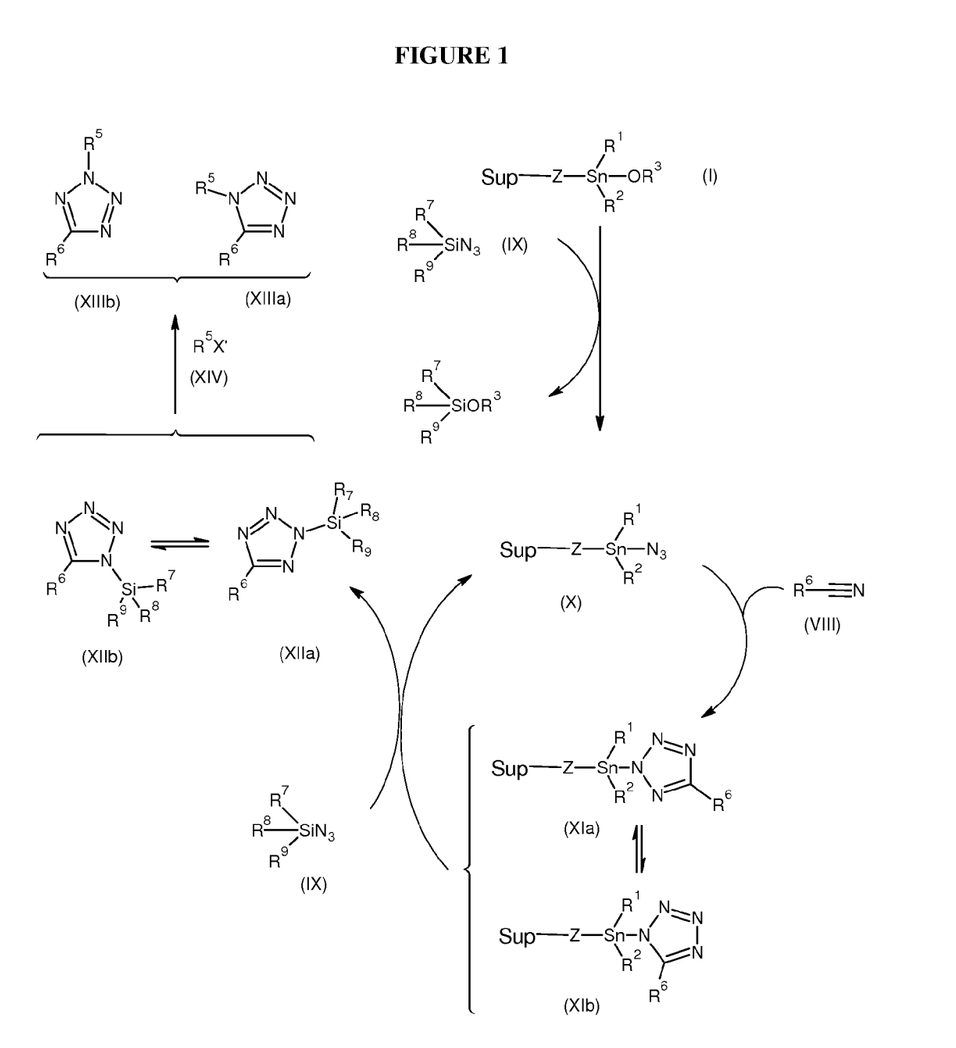
FIG. 1 shows the method of the present invention represented by reaction scheme 1.

This method can be represented by reaction scheme 1 shown in the appended FIG. 1 and from which it can be seen that the organotin compound of formula (I) reacts with a trialkylsilyl nitride of formula (IX) to give the reactive tin nitride of formula (X) which will then react with the nitrile of formula (VIII) according to a reaction of cycloaddition to give an intermediate of formula (XI) in which the radical $R^6$ has the same meaning as in formula (VIII) and the radicals $R^1$ and $R^2$ have the same meaning as in formula (I). The compound of formula (XI), in the presence of a second molecule of trialkylsilyl nitride of formula (IX), makes it possible on the one hand to regenerate the reactive species of formula (X) and to release the product of the reaction in the form of a silylated tetrazole of formulas (XIIa) or (XIIb) which then leads, in a last step, to a 5-substituted 1H-tetrazole of formula (XIIIa) or (XIIIb) in which $R^5$ is a hydrogen atom when a protodesilylation is carried out, or else to a 1,5-disubstituted tetrazole of formula (XIIIa) or (XIIIb) when $R^5$ is different from a hydrogen atom and the intermediate of formula (XIIa) or (XIIb) is reacted with a halide of formula (XIV).

The method according to the invention makes it possible to obtain molecules having a tetrazole function efficiently and economically since it uses a supported organotin azide in a transient manner, which makes it possible to overcome the drawbacks connected with purification of the end products while minimizing their contamination with organotin residues. In fact, at the end of the reaction, the compounds of formulas (XIIIa) or (XIIIb) and the tin compound of formula (X) can easily be separated, for example by simple filtration. The yields obtained can be very high (of the order of about 80 to 90% for the compounds where $R^6$=aryl) even though the reaction involves a reactant immobilized on a solid support and is carried out in heterogeneous phase. Moreover, the reactant of formula (I) can be used in a small amount since (X) is involved in the reaction as a catalyst, which, combined with its supported nature, allows very efficient eradication of the concentration of organotin residues in the tetrazoles synthesized.

The nature of the protective group mentioned for $R^5$ is not critical. It can be selected from the protective groups known by a person skilled in the art and as described by T P. G. M. Wuts, T. W. Greene, in "Greene's Protective Groups in Organic Synthesis", Wiley-Interscience, New York, 4$^{th}$ edition, 2006. Among these protective groups, we may notably mention the branched $C_3$-$C_4$ alkyl radicals such as tert-butyl; the $C_1$ or $C_2$ alkyl radicals that are mono-, di- or trisubstituted with phenyl, benzyl in which the aryl is unsubstituted or substituted with one or more groups selected from the $C_1$-$C_{12}$ alkyl radicals, hydroxyl, $C_1$-$C_{12}$ alkoxy, $C_1$-$C_{12}$ alkanoyloxy, halogen, nitro, cyano and trifluoromethyl; picolinyl, piperonyl; cumyl; allyl; cinnamoyl; fluorenyl; silyl such as $C_1$-$C_4$ trialkylsilyl for example trimethylsilyl, triethylsilyl and tert-butyldimethylsilyl or di-$C_1$-$C_4$-alkylphenylsilyl for example dimethylphenylsilyl; $C_1$-$C_{12}$ alkylsulfonyl; arylsulfonyl in which the phenyl ring is unsubstituted or substituted with one or more groups selected from the $C_1$-$C_{12}$ alkyl radicals, hydroxyl, $C_1$-$C_{12}$ alkoxy, $C_1$-$C_{12}$ alkanoyloxy, halogen, nitro, cyano, fluoroalkyl, trifluoromethyl; alkanoyl such as acetyl, valeroyl; $C_1$-$C_7$ alkanoyl for example methoxyl, ethoxyl or tert-butoxycarbonyl or allyloxycarbonyl.

The preferred protective groups are tert-butyl, benzyl, p-methoxybenzyl, 2-phenylpropyl, diphenylmethyl, di(p-methoxyphenyl)methyl, trityl, p-methoxyphenyl, diphenylmethyl, diphenyl-(4-pyridyl)methyl, benzyloxymethyl, methoxymethyl, ethoxymethyl, methylthiomethyl, 2-tetrahydropyranyl, allyl, trimethylsilyl and triethylsilyl.

The alkyl and alkoxy radicals mentioned as substituent for radical $R^6$ preferably have from 1 to 12 carbon atoms. Among such groups, we may mention in particular the methyl, methoxy, ethyl, ethyloxy, propyl, propyloxy, butyl and butyloxy groups. The linear, branched and cyclic alkyl radicals mentioned for $R^6$ can themselves optionally be substituted with one or more radicals selected from a halogen atom (chlorine, bromine, fluorine and optionally iodine) and the hydroxyl radicals, nitro, carboxyl alkyl, alkoxyl, aryl, alkenyl, alkynyl, alkoxycarbonyl, trifluoromethyl, fluoroalkyl, aminocarbonyl, sulfonyl and cyano.

As aryl radical mentioned for $R^6$, we may mention in particular the naphthyl, anthranyl, phenanthryl, o-tolyl, p-tolyl, xylyl, ethylphenyl, mesityl, phenyl, biphenyl, benzyl groups in which the naphthyl, anthranyl, phenanthryl, phenyl and benzyl aromatic nuclei can be substituted with one or more halogen atoms, and/or with one or more groups selected from the hydroxyl, nitro, carboxyl, carbonyl, alkyl, fluoroalkyl, trifluoromethyl, alkoxy, alkoxycarbonyl, amido, amino, nitro, cyano, carboxy, aryl, alkenyl, alkynyl radicals.

As heteroaryl radical mentioned for $R^6$, we may mention in particular the pyridyl, thienyl, furyl, bipyridyl, terpyridyl groups which can optionally be substituted with one or more halogen atoms, and/or with one or more groups selected from the hydroxyl, nitro, carboxyl, carbonyl, alkyl, fluoroalkyl, trifluoromethyl, alkoxy, silyloxy, alkoxycarbonyl, amido, amino, nitro, cyano, carboxy, aryl, alkenyl and alkynyl radicals.

Among the halogen atoms mentioned as substituent of radical $R^6$ of the compounds of formula (VIII), we may mention in particular chlorine, fluorine and bromine, chlorine being particularly preferred.

When $R^5$ is a hydrogen atom, the salts of the compounds of formula (XIIIa) or (XIIIb) are obtained by reacting the compound of formula (XIIIa) or (XIIIb) with a base. Among the addition salts obtained with a base, we may mention in particular the alkali metal salts, the ammonium salts and the salts of organic amines.

According to a preferred embodiment of the method according to the present invention, the alkyl radicals mentioned for the substituents $R^7$, $R^8$ and $R^9$ of the compounds of formula (IX) are selected from the methyl, ethyl, propyl, butyl radicals, the methyl radical being particularly preferred.

Among the compounds of formula (IX) above, those are preferred in which the radicals $R^7$, $R^8$ and $R^9$ are identical. A compound of formula (IX) that is particularly preferred according to the invention is the compound in which $R^7$=$R^8$=$R^9$=methyl (Me).

Among the compounds of formula (X), those in which $R^1$=$R^2$=methyl or ethyl are preferred.

According to a preferred embodiment of the method according to the invention, the compound of formula (I) is used in a catalytic amount. In the sense of the present invention, catalytic quality means an amount of catalyst preferably in the range from 0.05 mol % to 15 mol %.

The inert atmosphere in which the method according to the invention is carried out is preferably an atmosphere of argon or of dinitrogen.

According to a preferred embodiment of the invention, the first step of the method of preparing the compounds of formula (XIIIa) or (XIIIb) is carried out at a temperature that can vary from 130 to 140° C.

The organic solvent is preferably selected from dimethylformamide, dibutyl ether, diglyme, triglyme and the xylenes.

The duration of the first step can vary from 30 min to 20 hours; it is generally of the order of about 4 hours.

During the second step, hydrolysis of the compounds of formulas (XIIIa) or (XIIIb) in an acid medium is preferably carried out by adding, to the reaction mixture, an organic or inorganic acid, preferably selected from hydrochloric acid, sulfuric acid and trifluoroacetic acid.

At the end of the synthesis, the compound of formulas (XIIIa) or (XIIIb) obtained, in the liquid phase, can easily be separated from the organotin compound of formula (X) present in solid form in the reaction mixture, by any suitable technique known by a person skilled in the art, for example by filtration, decanting or sedimentation. The compound of formula (I) can then be regenerated for example by treatment with a strong base such as soda (in particular 4M NaOH in a 1:1 ethanol/water mixture) and then reaction with the reactant of formula (VI).

The expected compound of formulas (XIIIa) or (XIIIb) is then recovered after basic treatment of the reaction mixture, then acid treatment and crystallization from the aqueous phase.

Another object of the invention is the use of an alkoxylated organotin compound of formula (I) as defined above as catalyst for the heterogeneous-phase synthesis of a tetrazole selected from 5-phenyl-1H-tetrazole, 5-(4-methylphenyl)-1H-tetrazole, 5-(4-methoxyphenyl)-1H-tetrazole, 5-(3-methoxyphenyl)-1H-tetrazole, 5-(4-nitrophenyl)-1H-tetrazole, 4-(1H-tetrazol-5-yl)benzoic acid, 5-(3-chlorophenyl)-1H-tetrazole, 5-(4-chlorophenyl)-1H-tetrazole, 5-(4-hydroxyphenyl)-1H-tetrazole, 5-(3-trifluoromethylphenyl)-1H-tetrazole, 5-naphthyl-1H-tetrazole, 5-butyl-1H-tetrazole, 5-octyl-1H-tetrazole, 5-(2-bromophenyl)-1H-tetrazole and 5-biphenyl-2-yl-1H-tetrazole.

The present invention is illustrated by the following practical examples, but is not limited to these.

EXAMPLES

Raw materials used in the examples given below:
Chemicals: dimethyldichlorotin (CAS: 753-73-1), phenylmagnesium bromide (3.0 M in diethyl ether, diethyl ether, CAS: 100-58-3), lithium and aluminum hydride (CAS: 16853-85-3), diisopropylamine (CAS: 108-18-9), butyllithium (CAS: 109-72-8), tetrahydrofuran (CAS: 109-99-9), ethanol (CAS: 64-17-5), methanol (CAS: 67-56-1), hydrochloric acid (CAS: 7647-01-0), sodium chloride (7647-14-5), diiodine (CAS: 7553-56-2), sodium thiosulfate (CAS: 7772-98-7), diethyl ether (60-29-7), sodium sulfate (7487-88-9), sodium hydroxide (CAS: 1310-73-2), dimethyl carbonate (CAS: 616-38-6), these chemicals all marketed by the company Aldrich.

Crosslinked polystyrene beads, sold under the trade name Amberlite® XE 305 by the company Rohm and Haas or under the trade name PL-PS/DVB MP Resin by the company Polymer Laboratories;

Examples 1 to 12: Synthesis of 1H-Tetrazoles Substituted in Position 5 with an Aromatic Group In this example, 1H-tetrazoles substituted in position 5 with a substituted or unsubstituted phenyl group were prepared according to the following general reaction scheme:

consisting of reacting a catalyst of formula (I) (catalytic amount) with a trialkylsilyl nitride of formula (IX) and the nitrile of formula (VIII) corresponding to the tetrazole of formula (XIII) that we wish to obtain, under inert atmosphere under reflux in the organic solvent (n-butyl ether ($Bu_2O$)) for about 16 hours.

In situ, the catalyst of formula (I) reacts with the trialkylsilyl nitride of formula (IX) to give the corresponding reactive species of formula (X) (supported tin nitride) which will react with the nitrile of formula (VIII) used according to a reaction of cycloaddition to give the corresponding intermediate of formula (XI). The latter, in the presence of a second molecule of trialkylsilyl nitride of formula (IX), makes it possible on the one hand to regenerate the reactive species of formula (X) and on the other hand to release the product of the reaction in the form of a silylated tetrazole of formula (XII). After an acid treatment and then a basic treatment, the expected final tetrazole of formula (XIII) is easily obtained by aqueous phase crystallization and filtration.

The supported catalyst used in these examples is a catalyst of formula (I) with Z-1 for linkage in which n=4 and $R^1=R^2=R^3=CH_3$, and in which the insoluble solid support is polystyrene crosslinked with divinylbenzene.

Figure 2:
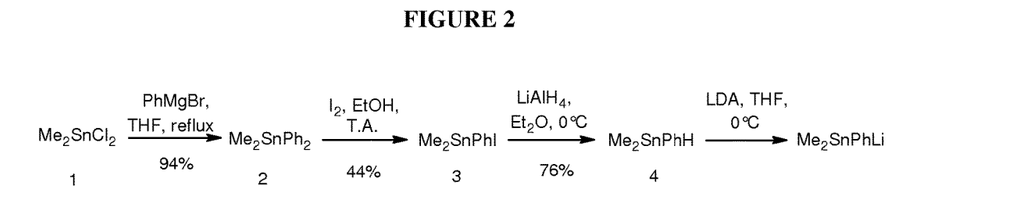
FIG. 2 shows reaction scheme 2.
Figure 3:
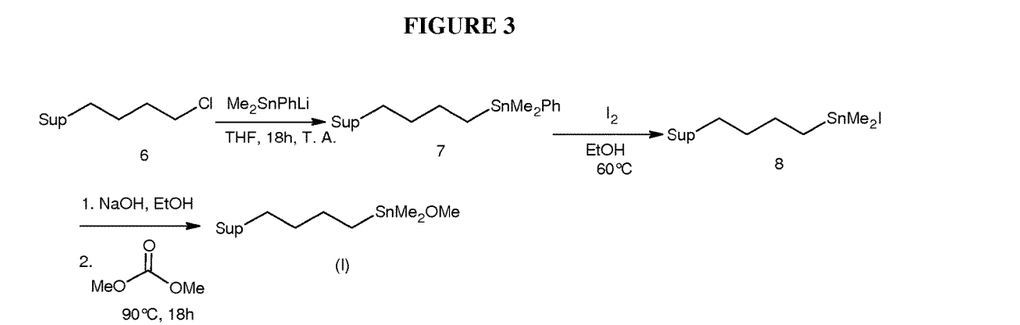
FIG. 3 shows reaction scheme 3.

It was synthesized according to reaction schemes 2 and 3 presented in the appended FIGS. 2 and 3 respectively:

1) Preparation of dimethyldiphenyltin 2

80.5 mmol of dimethyldichlorotin 1 ($Me_2SnCl_2$) in 120 mL anhydrous tetrahydrofuran (THF) was added dropwise and under argon to 70 mL of a solution of phenylmagnesium bromide (PhMgBr) at 2.3 M (161 mmol, 2 equivalents) in ethanol. The reaction mixture was heated at 80° C. for 3 hours and the reaction was monitored by thin-layer chromatography (TLC) to detect complete disappearance of the starting reactants. The reaction mixture was then hydrolyzed with 1M hydrochloric acid (HCl) (80 mL) and the aqueous phase was extracted with diethyl ether (3×150 mL). The organic phases were washed with NaCl (400 mL), dried over $MgSO_4$ and concentrated under vacuum. The residue was purified by silica gel chromatography and the expected compound 2 was obtained in the form of a colorless oil at a yield of 94%.

$^1$H NMR (300 MHz, CDCl$_3$) δ=0.51 (6H, s, $^2J^{117/119}{}_{Sn\text{-}H}$=56.6/58.8); 7.3-7.6 (10H, m) ppm.

$^{13}$C NMR (300 MHz, CDCl$_3$) δ=−9.7 ($^1J_{Sn\text{-}C}$=363); 128.6; 128.9; 136.6 ($^2J_{Sn\text{-}C}$=36); 141 ppm.

$^{119}$Sn NMR (300 MHz, CDCl$_3$) δ=−58.6 ppm.

2) Preparation of dimethylphenyltin iodide 3

A solution of iodine (3.19 g, 12.6 mmol, 1.02 eq.) in methanol (0.3M, 21 mL), was added in darkness, under argon and at room temperature, to a solution of 12.4 mmol of dimethyldiphenyltin 2 in methanol (0.3 M, 21 mL). The reaction mixture was stirred for 18 hours at room temperature and partially concentrated under vacuum. The resultant mixture was then diluted with a saturated aqueous solution of Na$_2$S$_2$O$_3$ and the aqueous phase was extracted with diethyl ether (3×200 mL). The organic phases were then washed with NaCl (300 mL), dried over MgSO$_4$ and concentrated under vacuum. The iodobenzene remaining in the resultant residue was distilled (boiling point at 0.68 mbar: 21.9° C.) and the expected compound 3 was obtained without any additional purification in the form of a yellow oil at a yield of 44%.

$^1$H NMR (300 MHz, CDCl$_3$) δ=1.05 (6H, s, $^2J^{117/119}{}_{SnH}$=55.4/58), 7.34-7.5 (3H, m), 7.6 (2H, d, $^3J$=7.6) ppm.

$^{119}$Sn NMR (300 MHz, CDCl$_3$) δ=−17 ppm.

3) Preparation of dimethylphenyltin hydride 4 (Me$_2$SnPhH)

17.6 mmol of compound 3 obtained above in the preceding step was added dropwise, at 0° C. under argon, to a suspension of 44.1 mmol of lithium aluminum hydride (LiAlH$_4$) (2.5 eq.) in 75 mL of ethanol. The reaction mixture was stirred for 2 hours at 0° C. in darkness and then hydrolyzed with 15 mL of water. The aqueous phase was extracted with diethyl ether (3×50 mL) and the organic phases were washed with a saturated solution of NaCl (40 mL), dried over MgSO$_4$ and concentrated under vacuum. Compound 4 was obtained in the form of a colorless oil at a yield of 76%.

$^1$H NMR (300 MHz, C$_6$D$_6$) δ=0.39 (6H, s, $^2J_{Sn\text{-}H}$=56), 5.66 (1H, s, $^1J^{117/119}{}_{SnH}$=11725/1810, SnH), 7.39 (3H, m), 7.62 (2H, d, $^3J$=7.3) ppm.

$^{13}$C NMR (300 MHz, C$_6$D$_6$) δ=−11 ($^2J_{Sn\text{-}C}$=351); 129.3; 137.3 ($^2J_{Sn\text{-}C}$=38.5), 137.8; 140 ppm.

$^{119}$Sn NMR (300 MHz, C$_6$D$_6$) δ=−121 ppm.

4) Preparation of poly[4-(dimethylphenylstannyl)butyl]styrene 7

27.7 mmol of compound 4 obtained above in the preceding step was added slowly, at 0° C. and under argon, to a solution of 30.5 mmol of lithium diisopropylamide (LDA) in anhydrous THF. The resultant mixture 5 was stirred for 1 hour at 0° C., then 7.4 g of polymer 6 in the dry state was added. The mixture was left to return to room temperature, then it was stirred for 18 hours. The resulting polymer was washed successively with 60 mL of a mixture of THF and water (1:1; v:v), 6×60 mL of THF, 4×60 mL of absolute ethanol before being dried under vacuum (0.5 mbar) at 60° C. for 5 hours. Polymer 7 was obtained in the form of a white resin (9.5 g).

$^{119}$Sn NMR MAS δ=−33 ppm.

5) Preparation of poly[4-(iododimethylstannyl)butyl]styrene 8

10.0 g of polymer 7 obtained above in the preceding step was added to a solution of iodine (3.81 g, 15.0 mmol) in 50 mL of absolute ethanol. The resultant mixture was stirred at 60° C. for 18 hours in darkness. The polymer was then washed successively with 60 mL of a mixture of THF/saturated aqueous solution of Na$_2$S$_2$O$_3$ (1:1; v:v), 6×60 mL of THF, 4×60 mL of absolute ethanol before being dried under vacuum (0.5 mbar) at 60° C. for 5 hours. Polymer 8 was obtained in the form of a pale yellow resin.

$^{119}$Sn NMR MAS δ=+49 ppm.

6) Preparation of Compound 9 (Reactant of Formula (I))

A 4 M solution of soda (2.36 mL, 9.5 mmol, 4 eq.) in an ethanol/water mixture (1:1; v:v) was added to a solution of 2 g (2.36 mmol) of polymer 8 obtained above in the preceding step in 10 mL of absolute ethanol. The reaction mixture was stirred at room temperature for 36 hours. The insoluble matter was washed successively with 4×30 mL of water, then 7×30 mL of ethanol before being dried under vacuum (0.5 mbar) at 60° C. for 5 hours. The resulting polymer was then put in a round-bottomed flask, to which 2 mL of dimethyl carbonate was then added. The reaction mixture was stirred for 18 hours at 90° C. After filtration, the expected reactant of formula (I) (compound 9) was washed with 70 mL of THF, and then with 70 mL of ethanol before being dried under vacuum (0.5 mbar) at 60° C. for 5 hours.

$^{119}$Sn NMR MAS δ=+110 ppm.

The synthesis of the various tetrazoles was then carried out as follows:

A two-necked flask equipped with a condenser was charged with the nitrile of formula (VIII) (1.0 mmol) corresponding to the expected tetrazole of formula (XIII), the reactant of formula (I) as prepared as indicated above (100 mg, 0.1 mmol) as well as (CH$_3$)$_3$SiN$_3$ (trimethylsilyl nitride (IX)) (0.2 mL, 1.5 mmol) in 2.5 mL of Bu$_2$O under inert atmosphere. The reaction mixture was heated under reflux under inert atmosphere for 16 hours and was then diluted in petroleum ether (10 mL) and treated with a 1M solution of NaOH (10 mL). The residual polymer was then filtered and washed successively with 1M NaOH (5 mL), THF (5 mL) and then petroleum ether (5 mL). The filtrate was recovered and the aqueous phase was separated and then acidified with HCl to pH 1 at 0° C. in order to crystallize the expected tetrazole of formula (XIII). The crystals were then filtered and dried under vacuum.

Table 1 below presents the various tetrazoles of formula (I) synthesized, as well as the yield of the reaction:

TABLE 1

| Example | Tetrazole of formula (VII) | Yield of product isolated (%) |
|---|---|---|
| 1 | 5-phenyl-1H-tetrazole | 95 |

TABLE 1-continued

| Example | Tetrazole of formula (VII) | Yield of product isolated (%) |
|---|---|---|
| 2 | 5-(4-methylphenyl)-1H-tetrazole | 91 |
| 3 | 5-(4-methoxyphenyl)-1H-tetrazole | 89 |
| 4 | 5-(3-methoxyphenyl)-1H-tetrazole | 78 |
| 5 | 5-(4-nitrophenyl)-1H-tetrazole | 90 |
| 6 | 4-(1H-tetrazol-5-yl)benzoic acid | 81 |
| 7 | 5-(3-chlorophenyl)-1H-tetrazole | 83 |
| 8 | 5-(4-chlorophenyl)-1H-tetrazole | 86 |
| 9 | 5-(4-hydroxyphenyl)-1H-tetrazole | 82 |
| 10 | 5-(3-trifluoromethylphenyl)-1H-tetrazole | 87 |
| 11 | 5-(2-bromophenyl)-1H-tetrazole | 72 |
| 12 | 5-biphenyl-2-yl-1H-tetrazole | 63 |

Characterization of the Compounds 5-phenyl-1H-tetrazole (Ex. 1)

White solid, Melting point: 210-211° C.;
$^1$H NMR (300 MHz, $d_6$-DMSO): δ=8.02-7.98 (m, 2H), 7.58-7.54 (m, 3H), ppm;
$^{13}$C NMR (75 MHz, $d_6$-DMSO): δ=155.8; 131.6; 129.8; 127.3; 124.7 ppm 5-(4-methylphenyl)-1H-tetrazole (Ex. 2)

White solid; Melting point.=246-248° C.
IR (KBr)=3100-2200 (Br), 1614, 1569, 1504, 1163, 1055, 1028, 823, 744 cm$^{-1}$
$^1$H NMR (300 MHz, $d_6$-DMSO): 7.92 ppm (d, J=8.0 Hz, 2H); 7.41 (d, J=8.0 Hz, 2H); 2.39 (s, 3H) ppm.
$^{13}$C NMR (100 MHz, $d_6$-DMSO): 155.0; 141.0; 129.8; 126.8; 121.2; 21.0 ppm.

5-(4-methoxyphenyl)-1H-tetrazole (Ex. 3)

White solid; Melting point: 231-233° C.
IR (KBr): 3200-2300 (Br), 1298, 1184, 1035, 750 cm$^{-1}$
$^1$H NMR (300 MHz, $d_6$-DMSO): δ=7.96 (d, J=9.0 Hz, 2H), 7.15 (d, J=9.0 Hz, 2H), 3.85 (s, 3H) ppm;
$^{13}$C NMR (100 MHz, $d_6$-DMSO): 161.3; 154.6; 128.5; 116.2; 114.7; 55.4 ppm 5-(3-methoxyphenyl)-1H-tetrazole (Ex. 4)

White solid
$^1$H NMR (300 MHz, $d_6$-DMSO): δ=7.64-7.50 (m, 2H), 7.53 (t, J=7.5 Hz, 1H), 7.17 (ddd, J=1.5 Hz, J=3 Hz, J=9 Hz, 1H)
$^1$H NMR (75 MHz, $d_6$-DMSO): δ=159.7; 130.7; 125.3; 119.1; 117.01; 112.1; 55.4 ppm.

5-(4-nitrophenyl)-1H-tetrazole (Ex. 5)

White solid, Melting point=218-220° C.
IR (KBr): 3500-2400 (Br), 1604, 1531, 1488, 1338, 1311, 993, 867, 854 cm$^{-1}$;

¹H NMR (300 MHz, d₆-DMSO): δ=8.45 ppm (d, J=9.0 Hz, 2H); 8.30 (d, J=9.0 Hz, 2H);

¹³C NMR (75 MHz, d₆-DMSO): δ=155.6; 148.8; 130.7; 128.3; 124.6 ppm.

4-(1H-tetrazol-5-yl)benzoic acid (Ex. 6)

¹H NMR (300 MHz, d₆-DMSO): δ=13.1 (s broad, 1H); 8.1 ppm (m, 4H); 3.3 (s broad, 1H)

¹³C NMR (75 MHz, d₆-DMSO): δ=166.6; 155.3; 132.9; 130.2; 128.2; 127.1

5-(3-chlorophenyl)-1H-tetrazole (Ex. 7)

¹H NMR (300 MHz, d₆-DMSO): 8.07-8.02 (m, 1H); 7.66-7.64 (m, 1H), 7.7-7.6 (m, 2H)

¹³C NMR (75 MHz, d₆-DMSO): 154.8; 133.9; 131.4; 130.9; 126.5; 126.4; 125.6

5-(4-chlorophenyl)-1H-tetrazole (Ex. 8)

White solid; Melting point: 252-254° C.;

¹H NMR (300 MHz, d₆-DMSO): δ=8.07 (d, J=8.8 Hz, 2H); 7.70 (d, J=8.8 Hz, 2H);

¹³C NMR (75 MHz, d₆-DMSO): δ=155.3; 136.3; 129.9; 129.0; 123.6.

5-(4-hydroxyphenyl)-1H-tetrazole (Ex. 9)

White solid, Melting point: 236-238° C.;

IR (KBr): 3600-3200 (Br), 1616, 1515, 1471, 1282, 1247, 1080, 995, 842 cm⁻¹;

¹H NMR (300 MHz, d₆-DMSO): δ=10.18 (Br s, 1H); 7.86 (d, J=8.5 Hz, 2H); 6.95 (d, J=8.5 Hz, 2H) ppm ¹³C NMR (75 MHz, d₆-DMSO): δ=160.0; 154.8; 128.7; 116.2; 114.6 ppm.

5-(4-trifluoromethylphenyl)-1H-tetrazole (Ex 10)

¹H NMR (300 MHz, d₆-DMSO): 8.35 (2H, m), 7.9 (1H, m), 7.85 (1H, m)

¹³C NMR (75 MHz, d₆-DMSO): 152.9; 128.5 (q, J=1.2 Hz); 128.5; 127.8 (q, J=32 Hz); 125.4 (q, J=3.8 Hz); 123.0; 121.3 (q, J=277 Hz); 121.0 (q, J=4.0 Hz).

5-(2-bromophenyl)-1H-tetrazole (Ex. 11)

White solid, melting point: 179-180° C.;

¹H NMR (300 MHz, d⁶-DMSO): 7.5-7.6 (m, 2H); 7.7 (dd, J=7.5; J=2, 1H);

¹³C NMR (100 MHz, d⁶-DMSO): 121.6; 126.3; 128.1; 131.9; 132.5; 133.4; 154.5.

5-biphenyl-2-yl-1H-tetrazole (Ex. 12)

White solid, melting point: 142-143° C.;

¹H NMR (300 MHz, d⁶-DMSO): 7.1 (m, 2H); 7.31 (m, 3H); 7.58 (m, 2H); 7.69 (m, 2H);

¹³C NMR (100 MHz, d⁶-DMSO): 123.4; 127.4; 127.5; 127.7; 128.2; 128.7; 130.5 (2C); 131.0; 139.2; 141.5.

Example 13: Preparation of 5-naphthyl-1H-tetrazole

In this example, 5-naphthyl-1H-tetrazole was prepared starting from the corresponding nitrile of formula (VIII) according to the protocol used above for the compounds in examples 1 to 12. 5-Naphthyl-1H-tetrazole was obtained in the form of a white solid at a yield of 85%.

Melting point: 205-206° C.;

IR (KBr): 3200-2200 (Br), 3060, 1566, 1417, 1249, 1085, 1020, 825, 759 cm⁻¹;

¹H NMR (300 MHz, d₆-DMSO): δ=8.57-8.54 (m, 1H), 8.21-8.18 (m, 1H); 8.11-8.08 (m, 1H); 8.00-7.98 (m, 1H); 7.74-7.63 (m, 3H);

¹³C NMR (75 MHz, d₆-DMSO): δ=133.3; 131.4; 129.9; 128.6; 128.3; 127.6; 126.7; 125.3; 125.1; 121.5; 114.4.

Example 14: Preparation of 5-butyl-1H-tetrazole

In this example, 5-butyl-1H-tetrazole was prepared starting from the corresponding nitrile of formula (VIII) according to the protocol used above for the compounds in examples 1 to 12. 5-Butyl-1H-tetrazole was obtained in the form of a white solid at a yield of 50%.

¹H NMR (300 MHz, d₆-DMSO): δ=2.87 (t, J=7.5 Hz, 2H); 1.68 (m, 2H); 1.33 (m, 2H); 0.9 (t, J=7.5 Hz, 3H).

¹³C NMR (75 MHz, d₆-DMSO): δ=155.9; 29.0; 22.3; 21.4; 13.4.

Example 15: Preparation of 5-octyl-1H-tetrazole

In this example, 5-octyl-1H-tetrazole was prepared starting from the corresponding nitrile of formula (VIII) according to the protocol used above for the compounds in examples 1 to 12. 5-Octyl-1H-tetrazole was obtained in the form of a pale yellow solid at a yield of 42%.

¹H NMR (300 MHz, d₆-DMSO): 2.85; (t, J=7.5 Hz, 2H); 1.68 (m, 2H); 1.26 (m, 10H); 0.85 (m, 3H).

¹³C NMR (75 MHz, d₆-DMSO): 155.9; 31.1; 28.4; 28.3; 27.0; 22.6; 22.0; 13.9.

The invention claimed is:

1. A method of heterogeneous-phase synthesis of tetrazoles, comprising carrying out said synthesis with an alkoxylated organotin compound as a catalyst, said alkoxylated organotin compound having the following formula (I):

(I)

in which:
Sup represents a macromolecular solid support;
Z represents a linkage between the macromolecular solid support Sup and the tin atom, Z being selected from the groups of the following formulas (Z-1) to (Z-6):

(Z-1)

(Z-2)

(Z-3)

(Z-4)

(Z-5)

(Z-6)

in which:
n and m, independently of one another, are integers in the range from 2 to 24,
o and p, independently of one another, are integers in the range from 2 to 24,
q is an integer in the range from 1 to 24,
$R^2$ and $R^3$, independently of one another, represent a linear $C_1$-$C_{24}$ alkyl radical, a branched or cyclic $C_3$-$C_{24}$ alkyl radical, linear $C_2$-$C_{24}$ alkenyl, branched or cyclic $C_3$-$C_{24}$ alkenyl, aryl or aralkyl.

2. The method as claimed in claim 1, wherein the synthesis is that of 5-substituted or 1,5-disubstituted tetrazoles.

3. A method of heterogeneous-phase synthesis of 5-substituted tetrazoles of the following formulas (XIIIa) and (XIIIb):

(XIIIa)

(XIIIb)

in which:
$R^6$ represents a linear $C_1$-$C_{24}$ alkyl, branched or cyclic $C_3$-$C_{24}$ alkyl, aryl, aralkyl or heteroaryl radical, substituted or unsubstituted;
$R^5$ represents a hydrogen atom or a protective group, wherein said method comprises:
1) at least one first step consisting of reacting, in an organic solvent, under inert atmosphere and at a temperature greater than or equal to 110° C., a nitrile of the following formula (VIII):

$$R^6\text{—CN} \qquad (VIII)$$

in which $R^6$ has the same meaning as that stated above for the compounds of formula (XIIIa) and (XIIIb), with a tin compound of the following formula (X):

(X)

in which:
Sup represents a macromolecular solid support,
Z represents a linkage between the macromolecular solid support Sup and the tin atom, Z being selected from the groups of the following formulas (Z-1) to (Z-6):

(Z-1)

(Z-2)

(Z-3)

(Z-4)

(Z-5)

(Z-6)

in which:
n and m, independently of one another, are integers in the range from 2 to 24,
o and p, independently of one another, are integers in the range from 1 to 24,
q is an integer in the range from 1 to 24,
$R^1$, $R^2$ and $R^3$, independently of one another, represent a linear $C_1$-$C_{24}$ alkyl radical or a branched or cyclic $C_3$-$C_{24}$ alkyl radical, linear $C_2$-$C_{24}$ alkenyl, branched or cyclic $C_3$-$C_{24}$ alkenyl, aryl or aralkyl, said reactant of formula (X) being generated in situ by reaction of the corresponding alkoxylated organotin reactant of formula (I):

(I)

and a trialkylsilyl compound of the following formula (IX):

(IX)

in which the radicals $R^7$, $R^8$ and $R^9$, which may be identical or different, represent a linear $C_1$-$C_{12}$ alkyl radical or a branched or cyclic $C_3$-$C_{12}$ alkyl radical, to obtain a tetrazole of the following formula (XIIa) or (XIIb):

(XIIa)

(XIIb)

in which $R^6$ has the same meaning as in formula (VIII) above and $R^7$, $R^8$ and $R^9$ have the same meaning as in formula (IX) above, after a reaction of exchange of the stannyl tetrazoles of the following formulas (XIa) or (XIb):

(XIa)

(XIb)

in which the radicals $R^1$, $R^2$ and $R^6$ have the same meanings as those stated above for the compounds of formulas (X) and (VIII) respectively, with the compound of formula (IX), and 2) at least one second step consisting:
i) either of hydrolyzing the compound of formulas (XIIa) or (XIIb) obtained above in step 1) in an acid medium, to obtain a compound of formulas (XIIIa) or (XIIIb) as defined above in which $R^5$ is a hydrogen atom, or
ii) to obtain a compound of formula (XIIIa) or (XIIIb) in which $R^5$ is different from a hydrogen atom, of reacting said compound of formula (XIIa) or (XIIb) obtained above in step 1) with a halide of the following formula (XIV):

X'—R⁵    (XIV)

in which X' is a halogen atom selected from chlorine and bromine and iodine and $R^5$ is a protective group, to obtain a compound of formulas (XIIIa) or (XIIIb) in which $R^5$ is a protective group.

4. The method as claimed in claim 3, wherein the compound of formula (I) is used in an amount ranging from 0.05 mol % to 15 mol %.

5. The method as claimed in claim 3, wherein the first step is carried out at a temperature in the range from 130 to 140° C.

6. The method as claimed in claim 3, wherein the organic solvent is selected from dimethylformamide, dibutyl ether, diglyme, triglyme and xylenes.

7. The method as claimed in claim 3, wherein the duration of the first step varies from 30 min to 20 hours.

8. The method as claimed in claim 3, wherein during the second step, hydrolysis of the compounds of formulas (XIIa) or (XIIb) in an acid medium is carried out by adding an acid selected from hydrochloric acid, sulfuric acid and trifluoroacetic acid to the reaction mixture.

9. Method for heterogeneous-phase synthesis of a tetrazole, said method comprising the steps of synthesis employing an alkoxylated organotin compound of formula (I):

(I)

in which:
Sup represents a macromolecular solid support;
Z represents a linkage between the macromolecular solid support Sup and the tin atom, Z being selected from the groups of the following formulas (Z-1) to (Z-6):

(Z-1)

(Z-2)

(Z-3)

(Z-4)

(Z-5)

-continued (Z-6)

in which:
n and m, independently of one another, are integers in the range from 2 to 24,
o and p, independently of one another, are integers in the range from 1 to 24,
q is an integer in the range from 1 to 24,
$R^1$, $R^2$ and $R^3$, independently of one another, represent a linear $C_1$-$C_{24}$ alkyl radical, a branched or cyclic $C_3$-$C_{24}$ alkyl radical, linear $C_2$-$C_{24}$ alkenyl, branched or cyclic $C_3$-$C_{24}$ alkenyl, aryl or aralkyl, as a catalyst,
wherein the tetrazole is selected from 5-phenyl-1H-tetrazole, 5-(4-methylphenyl)-1H-tetrazole, 5(4-methoxyphenyl)-1H-tetrazole, 5-(3-methoxyphenyl)-1H-tetrazole, 5-(4-nitrophenyl)-1H-tetrazole, 4-(1H-tetrazol-5-yl)benzoic acid, 5-(3-chlorophenyl)1H-tetrazole, 5-(4-chlorophenyl)-1H-tetrazole, 5-(4-hydroxyphenyl)-1H-tetrazole, 5-(3-trifluoromethylphenyl)-1H-tetrazole, 5-naphthyl-1H-tetrazole, 5-butyl-1H tetrazole, 5-octyl-1H-tetrazole, 5-(2-bromophenyl)-1H-tetrazole and 5-biphenyl-2yl-1H-tetrazole.

* * * * *

UNITED STATES PATENT AND TRADEMARK OFFICE
CERTIFICATE OF CORRECTION

PATENT NO. : 9,724,673 B2
APPLICATION NO. : 14/129355
DATED : August 8, 2017
INVENTOR(S) : Le Grognec et al.

It is certified that error appears in the above-identified patent and that said Letters Patent is hereby corrected as shown below:

In the Claims

Column 17, Claim 1, Line 48: The words "$R^2$ and $R^3$" after the words "range from 1 to 24," should read as "$R^{\wedge}1, R^2$ and $R^3$"

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*